US006280883B1

(12) United States Patent
Lamanna et al.

(10) Patent No.: US 6,280,883 B1
(45) Date of Patent: Aug. 28, 2001

(54) BIS (PERFLUORALKANESULFONYL)IMIDE SURFACTANT SALTS IN ELECTROCHEMICAL SYSTEMS

(75) Inventors: William M. Lamanna, Stillwater; Robert B. Loch, Woodbury; Alan D. Fanta, Minneapolis; Steven D. Boyd, Woodbury, all of MN (US); Hiroshi Shimada, Tokyo (JP); Phat T. Pham, Little Canada, MN (US); Bryan J. Johnson, Prescott, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/267,310

(22) Filed: Mar. 12, 1999

Related U.S. Application Data

(63) Continuation-in-part of application No. 08/988,507, filed on Dec. 10, 1997, now abandoned.

(51) Int. Cl.[7] .................................................. H01M 6/18
(52) U.S. Cl. ........................ 429/307; 429/199; 429/231.4; 429/231.1; 429/231.8; 252/62.2
(58) Field of Search .................................... 429/309, 314, 429/315, 316, 231.1, 231.8, 199, 231.4, 307; 252/62.2

(56) References Cited

U.S. PATENT DOCUMENTS

| 4,031,036 | 6/1977 | Koshar . | |
|---|---|---|---|
| 5,021,308 | 6/1991 | Armand et al. | 429/194 |
| 5,072,040 | 12/1991 | Armand | 564/82 |
| 5,162,177 | 11/1992 | Armand et al. | 429/194 |
| 5,437,944 | 8/1995 | Kita et al. | 429/195 |
| 5,502,251 | 3/1996 | Pohmer et al. | 564/82 |
| 5,652,072 | 7/1997 | Lamanna et al. | 429/198 |
| 5,827,602 | 10/1998 | Koch et al. | 429/194 |

FOREIGN PATENT DOCUMENTS

| 2239817 | 2/1974 | (DE) . |
|---|---|---|
| 0 466 483 A1 | 1/1992 | (EP) . |
| 2704099 A | 10/1994 | (FR) . |
| 05-062690 | 3/1993 | (JP) . |
| 05-326016 | 12/1993 | (JP) . |
| 07-282851 | 10/1995 | (JP) . |
| 08-335465 | 12/1996 | (JP) . |
| 09-092280 | 4/1997 | (JP) . |
| 09-106834 | 4/1997 | (JP) . |

OTHER PUBLICATIONS

Arai, J. et al., chemical abstract entitled "Secondary Lithium Batteries with Fluoro Surfactant Coated Electrodes", *Selects: Organofluorine Chemistry*, Issue 14, 127:20906u, p. 39 (1997).

DesMarteau, D., "Novel Perfluorinated Ionomers and Ionenes", *Journal of Fluorine Chemistry*, vol. 72, pp. 203–208 (1995).

Lemordant, D. et al., "Fluorinated Surfactants as Additives for Lithium Batteries", *Power Sources*, vol. 14, pp. 69–80 (1993).

Meussdoerffer, J.N. et al., "Bisperfluoroalkansulfonylimides $(R_fSO_2)_2NH$," *Chemiker Zeitung*, Vol. 96, No. 10, pp. 582–583 (Oct. 1972). (English translation attached).

Razaq, M. et al., "Oxygen Electroreduction in Perfluorinated Sulphonyl Imides", *Journal of Applied Electrochemistry*, vol. 17, pp. 1057–1064 (1987).

(List continued on next page.)

*Primary Examiner*—Laura Weiner
(74) *Attorney, Agent, or Firm*—Daniel C. Schulte; Robert H. Jordan

(57) ABSTRACT

Electrolyte compositions and electrochemical systems containing such compositions are described where the electrolyte includes in a matrix material a combination of a conductive salt and a bis(perfluoroalkanesulfonyl)imide surfactant salt. The compositions improve wettability of electrodes and separators while maintaining and improving conductivity, stability, and compatibility with other cell components.

41 Claims, 1 Drawing Sheet

OTHER PUBLICATIONS

Razaq, M. et al., "Perfluorosulfonimide as an Additive in Phosphoric Acid Fuel Cell", *J. Electrochem. Soc.*, vol. 136, No. 2, pp. 385–390 (Feb. 1989).

"Stable, Electroinactive Wetting Agent for Fuel Cells", *NASA Tech Briefs*, p. 56 (Dec. 1994).

Tudela Ribes, A. et al., "Correlation Between Cycling Efficiency and Surface Morphology of Electrodeposited Lithium, Effect of Fluorinated Surface Active Additives", *Journal of Power Sources*, vol. 58, pp. 189–195 (1996).

BIS (PERFLUORALKANESULFONYL)IMIDE SURFACTANT SALTS IN ELECTROCHEMICAL SYSTEMS

CROSS-REFERENCE TO RELATED APPLICATION

This is a continuation-in-part of application Ser. No. 08/988,507 of Dec. 10, 1997 now abandoned.

FIELD OF THE INVENTION

This invention relates to bis(perfluoroalkanesulfonyl) imide surfactant salts which, when used in electrolytes, enable the electrolytes to quickly and effectively wet the electrodes and separator of an electrochemical system. This invention further relates to the surfactant salts used with short chain bis(perfluoroalkane)imide conductive salts to improve the safety and performance of a battery.

BACKGROUND OF THE INVENTION

In recent years, highly conductive lithium salts such as lithium perchlorate, lithium hexafluorophosphate, lithium tetrafluoroborate, lithium hexafluoroarsenate and lithium trifluoromethanesulfonate, lithium bis(trifluoromethanesulfonyl)imide, lithium bis(perfluoroethanesulfonyl)imide and lithium tris(trifluoromethanesulfonyl)methide have found frequent use in liquid, polymer and gel electrolytes for lithium primary and secondary batteries. See, for example, Kirk-Othmer's *Encyclopedia of Chemical Technology*, Fourth Edition, 3, 1016–1018 (1992) and 1107–1109; and 15, 446–447 (1995). Typically, liquid electrolytes for lithium batteries are made by dissolving lithium salt(s) of choice in anhydrous polar aprotic liquid solvent(s) at a $Li^+$ molar concentration of around 0.5–2.0 M to produce a homogeneous solution having good conductivity and stability. The solvent must be sufficiently polar to effectively dissolve and dissociate the electrolyte salt, yet the solvent must be aprotic, i.e., free of any active hydrogen, to prevent reaction with the anode, which contains lithium metal or a form of carbon, such as graphite, intercalated with lithium. Liquid electrolytes are often very viscous, due to extensive polar interaction, and have a very high surface tension, exceeding 40 dynes/cm.

The liquid electrolyte is normally imbibed into the battery during the last part of its construction, and it is desirable that the electrodes and separator be quickly and thoroughly wet by the electrolyte so as to facilitate rapid battery manufacturing and to optimize battery performance. However, due to high viscosity and surface tension, the liquid electrolyte often cannot wet the separator or composite electrodes quickly and effectively. Separators are typically constructed from microporous polyolefin films which can have a surface energy as low as 30–35 dynes/cm. Electrodes are also frequently constructed from hard-to-wet (i.e., low surface energy) materials, including polytetrafluoroethylene and polyvinylidene fluoride binders. The very small size and tight construction of most lithium batteries (typically button, jelly-roll or prismatic configurations) further aggravates the wetting problem.

The relative surface energy between a liquid and a porous solid is very important in determining the wetting properties of the liquid. A liquid with a surface energy higher than the surface energy of the solid substrate will not wet the solid. The liquid will bead on the surface of the solid. A liquid with a surface energy approximately equal to the surface energy of the solid substrate will wet the solid but at a slow rate of penetration and will only penetrate the larger pores of the solid. A liquid with a surface energy lower than that of the solid substrate will rapidly wet the solid and penetrate substantially all of the open porosity of the solid. Therefore in order to effect complete and rapid wetting of the separator and electrode materials of a battery, the surface energy of the liquid should be less than the surface energy of the solid materials. These wetting properties apply not only to pure liquids but also to materials with liquid phases such as plasticized polymers.

Many tradeoffs are made in battery design and process engineering in order to accommodate the necessity of a complete and rapid electrolyte fill operation. For example, the electrodes cannot be manufactured to minimize porosity because at some point the pore size will be too small to be effectively wetted by electrolyte. Yet the lower the porosity of the electrode the more active material that can be packed into the cell and the higher the resulting energy of the battery. As a result, increasing the wetting properties of an electrolyte will allow the use of electrodes with higher density and energy.

Many of the electrolyte formulations available have a surface energy, which is too high to spontaneously wet the battery components. These formulations must be compromised with suitable solvents, which decrease the performance characteristics of the battery. The use of a surfactant will allow the use of electrolyte solvent formulations not previously accessible to the battery engineer.

Special process techniques are sometimes employed such as vacuum or pressure to accelerate the wetting of components by the electrolyte. Increasing the wetting properties of the electrolyte can minimize or eliminate these techniques and can decrease the time necessary for the electrolyte fill operation.

The availability of a compatible surfactant salt opens up a wider range of operating parameters for the battery engineer in the design and manufacture of components, selection of materials, and formulation of electrolytes.

Conventional surfactants which aid electrolyte wetting can have an adverse effect on cell performance, due to their inherent thermal or redox instability, their interference with conductivity, or their incompatibility with other cell components such as the anode, cathode or current collector.

Thus, there remains a need to improve the wetting of battery electrodes and separators by a non-aqueous liquid electrolyte while maintaining the desired stability and compatibility of the liquid electrolyte with other cell components.

SUMMARY OF THE INVENTION

We have found that use of certain fluorinated imide surfactant salts in electrolyte compositions exhibits improved wetting of electrodes and separators while maintaining and/or improving conductivity, stability and compatibility with other cell components in electrochemical systems, such as batteries, double-layer capacitors, fuel cells, electroplating, electrorefining and the like.

Accordingly, the present invention provides for an improved electrolyte composition which includes:

(a) a conductive salt including a cation selected from the group consisting of an alkali metal; an alkaline earth metal; a Group IIB metal; a Group IIIB metal; a transition metal; a rare earth metal; a nitrogen onium cation, such as tetraalkylammonium, trialkylammonium, N-alkylpyridinium and N,N'- dialkylimidazolium, in which alkyl has 1 to 4 carbon atoms; and a proton; and an anion selected from the group consisting of $R_f^0SO_3^-$; in which $R_f^0$ is a perfluoroalkyl group having between 2 and 4 carbon atoms;

an anion of the formula:

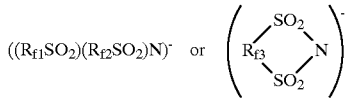

in which $R_{f1}$ and $R_{f2}$ are each independently a straight or branched perfluoroalkyl group of 1 to 4 carbon atoms, with $R_{f1}$ and $R_{f2}$ having a total of up to 5 carbon atoms;

and $R_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms;

an anion having a formula $R_{f4}R_{f5}N-(CF_2)_n,SO_2-X$;

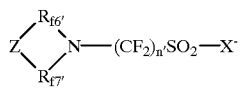

in which $X^-$ is $-O^-$, $-N^-SO_2R_{f4'}$ or

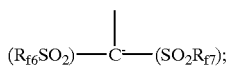

Z is $-CF_2-$, $-O-$,

or $-SF_4-$; $R_{f4}$, $R_{f4'}$, and $R_{f5}$, independently, are $-C_mF_{2m+1}$, or $-(CF_2)_q-SO_2-X^-$; $R_{f6}$ and $R_{f7}$, independently, are $-C_mF_{2m+1}$, $-(CF_2)_4-SO_2-X^-$,

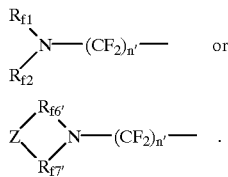

$R_{f8}$ is $-C_mF_{2m+1}$, or $-(CF_2)_q-SO_2-X^-$; $R_{f6'}$ and $R_{f7'}$, independently, are perfluoroalkylene moieties having the formula $-C_rF_{2r}-$; n' is 1–4; r is 1–4; m is 1–4; and q is 1–4;

a bis-fluoroalkylsulfonyl methide anion $R_f^{II}-SO_2-C^-(R)-SO_2-R_f^{II}$ in which $R_f^{II}$ and $R_f^{III}$, independently, are perfluoroalkyl groups having between 1 and 4 carbon atoms, wherein the sum of $R_f^{II}$ and $R_f^{III}$ is up to 5 carbon atoms, and R is H, CN, F, alkyl of 1 to 6 carbon atoms, phenyl or phenyl substituted by alkyl of 1 to 4 carbon atoms;

and a tris-(perfluoroalkanesulfonyl)methide anion of the formula: $^-C(SO_2R_f^{II})(SO_2R_f^{III})(SO_2R_f^{IV})$ in which $R_f^{II}$, $R_f^{III}$, and $R_f^{IV}$, independently, are perfluoroalkyl groups having between 1 and 4 carbon atoms, wherein the sum of $R_f^{II}$, $R_f^{III}$ and $R_f^{IV}$ are up to 6 carbon atoms, and (b) a surfactant salt of the formula

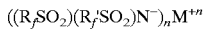

wherein $M^{+n}$ is a cation with a valence equal to n;

n is from 1 to 4;

$R_f$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms on the alkyl chain, which perfluoro(cyclo)alkyl, or perfluoroalkyl chain may optionally contain catenary heteroatoms; and $R_f'$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms on the alkyl chain, which perfluoro(cyclo)alkyl, or perfluoroalkyl chain may optionally contain catenary heteroatoms, wherein $R_f$ and $R_f'$ taken together have a total of at least 8 carbon atoms; and wherein the molar ratio of conductive salt to surfactant salt is between about 99.9:0.1 to about 75:25.

In a second aspect, the invention features an electrochemical system that includes at least one positive electrode, at least one negative electrode, and an electrolyte comprising the combination of a conductive salt and a surfactant salt as described above, where the molar ratio of conductive salt to surfactant salt may range between about 99.9:0.1 to 75:25, preferably between about 99:1 to 90:10.

A third aspect of the invention includes a method of improving wetting of electrodes and separators in electrochemical systems by incorporating into an electrolyte composition in a matrix material containing a conductive salt up to 25 mole %, based on total salt content, of a fluorinated imide surfactant as described above.

We have found that by adding a surfactant salt of the present invention to a conductive salt in an electrolyte composition, one or more of the following advantages can result:

provides all of the requisite functions of a battery electrolyte salt including: solubility, ionic conductivity, chemical and thermal stability, etc.;

lowers the surface tension of the resulting electrolyte solution;

allows wetting of battery component materials such as separators and electrodes which would not normally wet-out in available solutions;

expands the range of electrolyte compositions available by allowing the use of high viscosity, high surface energy solvents;

allows more rapid wetting of battery components to save time, process steps, and process equipment;

increases the area of contact between the electrolyte and the electroactive materials to decrease battery internal resistance and increase performance;

can be used in small quantity additions to existing electrolyte formulations to enhance performance; and provides for potential applications in a variety of battery systems including aqueous electrolyte batteries as well as fuel cells and capacitors.

Surprisingly, we have further found that in lithium ion battery electrolytes comprising short chain bis (perfluoroalkanesulfonyl)imide conductive salts, preferably bis(perfluoroethanesulfonyl)imide conductive salts, incorporation of surfactant salts of this invention, preferably at concentrations of 10% by weight or more based on the weight of the conductive salt, greatly improves the safety and performance of the battery.

Lithium ion battery safety is a critical issue, due to the potential of the highly reactive battery components to undergo thermal runaway and resultant battery explosion. Graphite electrodes which are intercalated with lithium (i.e., lithiated graphite) have similar chemical and electrochemical characteristics to lithium metal. As such, these electrodes are very reactive and exhibit an exothermic reaction with the electrolyte at elevated temperatures, temperatures which may be encountered in the battery under severe use conditions or during an electrical short. Incorporating long chain perfluorinated imide surfactant salts of this invention in electrolytes comprising short chain bis(perfluoroalkanesulfonylimide) conductive salts greatly reduces exotherm energies produced at the electrode/electrolyte interface when such a battery reaches temperatures of up to 200° C.

Battery performance is another critical issue, as measured by good electrolyte conductivity, high repassivation potential, and minimal capacity fade during high temperature storage and/or cycling. Incorporating surfactant salts of this invention into electrolytes comprising short chain bis(perfluoroalkanesulfonylimide) conductive salts maintains the high ionic conductivity of the electrolyte. Corrosion of aluminum current collectors is greatly reduced when employing a surfactant salt, as repassivation potential of the cell is increased to over 4.5 volts, thus greatly reducing the corrosion current at high positive potentials. When employing a surfactant salt, capacity fade in cells during high temperature cycling and storage (e.g., 60° C. or higher at full charge of 4.2 V) is reduced when compared to similar cells containing no surfactant salt. Overall, this surfactant salt/conductive salt combination gives electrolyte salt performance comparable to $LiPF_6$, without the drawbacks of hydrolytic and thermal instability inherent in the $PF_6^-$ anion.

Thus, a further aspect of the present invention includes a method of improving the safety and performance of an electrochemical system, e.g. a battery or rechargeable battery, particularly a lithium ion battery, by employing an electrolyte composition which incorporates an effective amount or more of a fluorinated imide surfactant as described above containing a conductive salt having a cation as described above, but preferably lithium, and an anion of the formula:

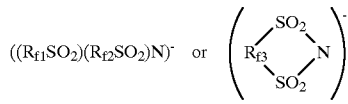

in which $R_{f1}$ and $R_{f2}$ are each independently a straight or branched perfluoroalkyl group of 1 to 4 carbon atoms, with $R_{f1}$ and $R_{f2}$ taken together having a total of up to 5 carbon atoms; $R_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms.

DETAILED DESCRIPTION

Figure 1:
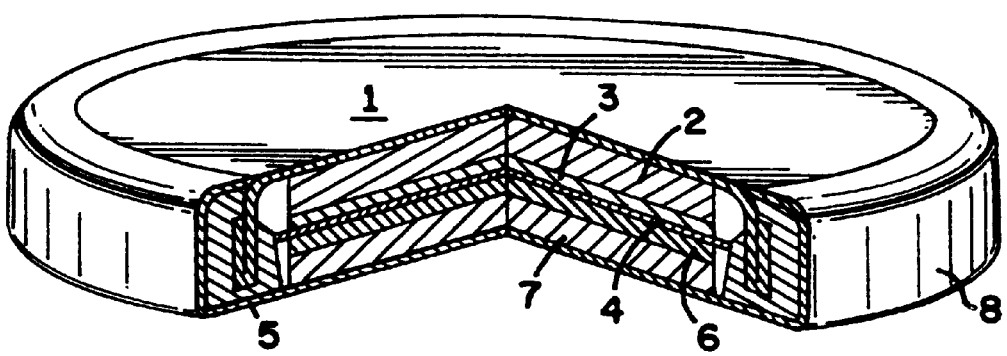
FIG. 1 is a cut-away view of a lithium-ion battery.

The present invention relates to electrolyte compositions useful in electrochemical systems such as batteries, e.g. primary and secondary (rechargeable) batteries, double-layer capacitors, supercapacitors, fuel cells, electroplating and electrorefining systems and the like. The electrolyte compositions include combinations of certain fluorinated imide surfactant salts which exhibit improved wetting of electrodes and separators along with good conductivity, stability and compatibility with other cell components.

The fluorinated imide surfactant salts useful in this invention are depicted by the formula:

wherein:

$M^{+n}$ is a cation with valence equal to n;

n is from 1 to 4;

$R_f$ is a straight or branched perfluoroalkyl group of 1 to 12 carbon atoms, preferably 4 to 12 carbon atoms, a perfluorocycloalkyl group or a perfluorocycloalkyl perfluoroalkyl group of 4–7 ring carbon atoms and 1–4 carbon atoms on the alkyl chain, and which perfluoro(cyclo)alkyl or perfluoroalkyl chain may also contain catenary heteroatoms such as oxygen and nitrogen; and $R_f'$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms on the alkyl chain, and which perfluoro(cyclo)alkyl or perfluoroalkyl chain may also contain catenary heteroatoms such as oxygen and nitrogen;

wherein the sum of carbon atoms in the $R_f$ and $R_f'$ chains must be at least 8.

Preferably, $M^{+n}$ is a cation of an alkali metal, an alkaline earth metal, a transition metal, a rare earth metal, a Group IIB metal or a Group IIIB metal, a nitrogen onium cation, or a proton; more preferably, $M^{+n}$ is a cation of an alkali metal; most preferably, $M^{+n}$ is a lithium cation.

Suitable fluorinated lithium imide surfactant salts include $(C_8F_{17}SO_2)N^-(SO_2CF_3)Li^+$, $(C_4F_9SO_2)_2N^-Li^+$, $(C_8F_{17}SO_2)N^-(SO_2C_4F_9)Li^+$, and $[(CF_3)_2NCF_2CF_2SO_2]_2N^-Li^+$. Other cations may replace the lithium cation, such as $Na^+$, $Ca^{+2}$, $Ba^{+2}$, $Al^{+3}$, $La^{+3}$, $Eu^{+3}$, $Sm^{+3}$, and $H^+$. A nitrogen onium cation includes for example, a tetraalkylammonium, trialkylammonium, N-alkyl-pyridinium and an N,N'-dialkylimidazolium in which alkyl has 1 to 4 carbon atoms, such as $(C_2H_5)_4N^+$, $(CH_3)_4N^+$,

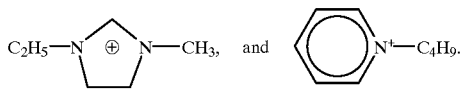

The electrolyte composition of the present invention includes a conductive salt different from the surfactant salt. Typically any conventional conductive salt known for electrochemical systems may be used. For example, a conductive salt may include:

a cation selected from the group consisting of an alkali metal; an alkaline earth metal; a Group IIB metal; a Group IIIB metal; a transition metal; a rare earth metal; a nitrogen onium cation such as tetraalkylammonium, trialkylammonium, N-alkylpyridinium and N,N'-dialkylimidazolium; and a proton; and an anion selected from the group consisting of $R_f^oSO_3^-$; in which $R_f^o$ is a perfluoroalkyl group having between 2 and 4 carbon atoms;

an anion of the formula:

$$((R_{f1}SO_2)(R_{f2}SO_2)N)^- \quad \text{or} \quad \left( \begin{array}{c} SO_2 \\ R_{f3} \diagup \diagdown N \\ \diagdown SO_2 \diagup \end{array} \right)^-$$

in which $R_{f1}$ and $R_{f2}$ are each independently a straight or branched perfluoroalkyl group of 1 to 4 carbon atoms, with $R_{f1}$ and $R_{f2}$ having a total of up to 5 carbon atoms;

and $R_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms;

an anion having a formula $R_{f4}R_{f5}N-(CF_2)_n\cdot SO_2-X^-$;

$$Z \diagup\!\!\!\!\! \begin{array}{c} R_{f6'} \\ N-(CF_2)_{n'}SO_2-X^- \\ R_{f7'} \end{array}$$

in which $X^-$ is $-O^-$, $-N^-SO_2R_{f4'}$ or $$(R_{f6}SO_2)-\overset{|}{\underset{|}{C}}-(SO_2R_{f7});$$

Z is $-CF_2-$, $-O-$, $$-\overset{|}{\underset{|}{NR_{f8}}},$$

or $-SF_4-$; $R_{f4}$, $R_{f4'}$ and $R_{f5}$, independently, are $-C_mF_{2m+1}$, or $-(CF_2)_q-SO_2-X^-$; $R_{f6}$ and $R_{f7}$, independently, are $-C_mF_{2m+1}$, $-(CF_2)_4-SO_2-X^-$, $$\begin{array}{c} R_{f1} \\ \diagdown \\ N-(CF_2)_{n'}- \\ \diagup \\ R_{f2} \end{array} \quad \text{or}$$

$$Z \diagup\!\!\!\!\! \begin{array}{c} R_{f6'} \\ N-(CF_2)_{n'}- \\ R_{f7'} \end{array}.$$

$R_{f8}$ is $-C_mF_{2m+1}$, or $-(CF_2)_q-SO_2-X^-$; $R_{f6'}$ and $R_{f7'}$, independently, are perfluoroalkylene moieties having the formula $-C_rF_{2r}-$; n' is 1–4; r is 1–4; m is 1–4; and q is 1–4;

a bis-fluoroalkylsulfonyl methide anion $R_f{}^{II}-SO_2-C^-(R)-SO_2-R_f{}^{III}$ in which $R_f{}^{II}$ and $R_f{}^{III}$, independently, are perfluoroalkyl groups having between 1 and 4 carbon atoms, wherein the sum of $R_f{}^{II}$ and $R_f{}^{III}$ is up to 5 carbon atoms and R is H, CN, F, alkyl of 1 to 6 carbon atoms, phenyl or phenyl substituted by alkyl of 1 to 4 carbon atoms;

and a tris-(perfluoroalkanesulfonyl)methide anion of the formula: $^-C(SO_2R_f{}^{II})(SO_2R_f{}^{III})(SO_2R_f{}^{IV})$ in which $R_f{}^{II}$, $R_f{}^{III}$, and $R_f{}^{IV}$, independently, are perfluoroalkyl groups having between 1 and 4 carbon atoms, wherein the sum of $R_f{}^{II}$, $R_f{}^{III}$ and $R_f{}^{IV}$ are up to 6 carbon atoms.

A more preferred conductive salt includes one that has a $(CF_3SO_2)_3C^-$ anion, or has an anion of the formula:

$$((R_{f1}SO_2)(R_{f2}SO_2)N)^- \quad \text{or} \quad \left( \begin{array}{c} SO_2 \\ R_{f3} \diagup \diagdown N \\ \diagdown SO_2 \diagup \end{array} \right)^-$$

or has an anion of the formula:

$$R_f{}^V SO_3^-$$

in which $R_{f1}$ and $R_{f2}$ are each independently a straight or branched perfluoroalkyl group of 1 to 4 carbon atoms, with $R_{f1}$ and $R_{f2}$ having a total of up to 5 carbon atoms;

$R_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms; and $R_f{}^V$ is a perfluoroalkyl group having from 2 to 4 carbon atoms.

Most preferred conductive salts are lithium bis(perfluoromethanesulfonyl)imide, lithium perfluoroethanesulfonate, lithium tris(perfluoromethanesulfonyl)methide, lithium bis(perfluoroethanesulfonyl)imide, lithium (perfluorobutanesulfonyl)(perfluoromethanesulfonyl)imide, lithium perfluorobetane sulfonate, or a mixture thereof.

A particularly preferred electrolyte composition of the present invention involves incorporating, preferably at concentrations of 10% by weight or more based on the weight of the conductive salt, a fluorinated imide surfactant as described above in combination with a matrix material containing a conductive salt having a cation, as described above, preferably lithium, and an anion of the formula:

$$((R_{f1}SO_2)(R_{f2}SO_2)N)^- \quad \text{or} \quad \left( \begin{array}{c} SO_2 \\ R_{f3} \diagup \diagdown N \\ \diagdown SO_2 \diagup \end{array} \right)^-$$

in which $R_{f1}$ and $R_{f2}$ are each independently a straight or branched perfluoroalkyl group of 1 to 4 carbon atoms, with $R_{f1}$ and $R_{f2}$ having a total of up to 5 carbon atoms;

$R_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms. A preferred conductive salt is lithium bis(perfluoroethanesulfonyl)imide, or lithium(perfluorobutanesulfonyl)(perfluoromethanesulfonyl)imide.

This particular electrolyte composition has been found especially effective in improving the safety (i.e., preventing thermal runaway) and performance (i.e., excellent electrolyte conductivity, high repassivation potential, and minimal capacity fade during high temperature storage and/or cycling) of lithium ion batteries.

In general, the above described low and high molecular weight bis(perfluoroalkanesulfonyl)imide and cyclic perfluoroalkylenedisulfonylimide conductive and surfactant salts can be prepared from the reaction of perfluoroalkanesulfonyl fluorides, e.g. $R_fSO_2F$, or perfluoroalkylenedisulfonyl fluoride, $FSO_2R_{f3}SO_2F$, with anhydrous ammonia. Symmetrical imides in which $R_f$ and $R_f{}'$ and $R_{f1}$ and $R_{f2}$ are the same can be prepared in a single step using a non-nucleophilic base such as triethylamine as shown in Scheme I, whereas unsymmetrical imides in which $R_f$ and $R_f'$ and $R_{f1}$ and $R_{f2}$ are different must be prepared in two steps as shown in Scheme II.

SCHEME I

SCHEME II

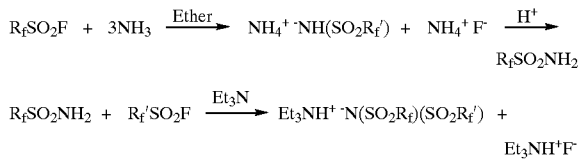

Cyclic perfluoroalkylenedisulfonylimide salts can be prepared as described in U.S. Pat. No. 4,387,222, incorporated herein by reference.

Perfluoroalkanesulfonyl fluorides and perfluoroalkylenedisulfonyl fluorides used as precursors to the imide salts of this invention can be prepared by a variety of methods known in the art as described, for example, in U.S. Pat. Nos. 3,542,864; 5,318,674; 3,423,299; 3,951,762; 3,623,963; 2,732,398, S. Temple, *J. Org. Chem.*, 33(1), 344 (1968), and D. D. DesMarteau, *Inorg. Chem.*, 32, 5007 (1993), all of which are incorporated herein by reference.

To form the electrolyte composition, the conductive and surfactant salts are, optionally, mixed together with a matrix material, such that the salts are at least partially dissolved or dispersed in each other or in the matrix material. The salts are preferably employed at a concentration such that the conductivity of the electrolyte solution is at or near its maximum value, although a wide range of other concentrations will also serve.

An electrolyte composition may contain as high as 100% total salt concentration where the mixture of conductive and surfactant salts are inherently liquid at ambient temperature, e.g. 20° C. or higher. Such "ionic liquid electrolytes" are described in U.S. Pat. No. 5,827,602 which reference is incorporated herein. Such ionic liquids find application in electrochemical systems such as non-aqueous batteries, electrochemical capacitors, electroplating, and the like.

A matrix material may be used to dissolve the salts and may be in the form of a solid, liquid, gel or a liquid impregnated porous membrane. For battery applications, the matrix material is chosen to provide the particular conductance, viscosity, mechanical strength, reactivity and stability desired for the electrolyte.

Suitable matrix materials for preparing electrolyte solutions can be liquid, polymeric or mixtures of polymer and liquid. Examples of suitable solid matrix materials include polymers and copolymers such as polyethers like poly (ethylene oxide), polyesters, polyacrylates, polyphosphazenes, polysiloxanes, poly(propylene oxide), fluoropolymers (e.g., poly(vinylidene fluoride)), and poly (acrylonitrile), as well as the polymers and copolymers described in Armand et al., U.S. Pat. No. 4,505,997, incorporated herein by reference, and mixtures thereof. The polymers may be used in cross-linked or uncross-linked form and plasticized. Such materials are generally dry, i.e., have a water content less than about 100 ppm, preferably less than about 50 ppm.

Mixtures of matrix materials can be employed and are sometimes preferred in tailoring the matrix material's properties to provide optimum performance. In general, the amount of matrix material is selected such that the total salt concentration ranges from about 0.1 M (moles per liter) to about 2.0 M, preferably about 1 M. Preferably, the conductive salt concentration in the electrolyte is from about 0.5 to 1.5 M, and the surfactant salt concentration in the electrolyte is from about 10 to 250 millimoles per liter.

In batteries comprising a highly reducing electrode (such as lithium metal) and a liquid matrix material, the liquid is preferably a nonaqueous, polar, aprotic, organic solvent. Such liquids are generally dry, i.e., have a water content less than about 100 ppm, preferably less than about 50 ppm. Examples of suitable aprotic liquids include linear ethers such as diethyl ether, diethylene glycol dimethyl ether, and 1,2-dimethoxyethane; cyclic ethers such as tetrahydrofuran, 2-methyltetrahydrofuran, dioxane, dioxolane, and 4-methyldioxolane; esters such as methyl formate, ethyl formate, methyl acetate, dimethyl carbonate, diethyl carbonate, propylene carbonate, ethylene carbonate, and butyrolactones (e.g. gamma butyrolactone); nitriles such as acetonitrile and benzonitrile; nitro compounds such as nitromethane or nitrobenzene; amides such as N,N-dimethylformamide, N,N-diethylformamide, and N-methylpyrrolidinone; sulfoxides such as dimethyl sulfoxide; sulfones such as dimethylsulfone; tetramethylene sulfone, and other sulfolanes; oxazolidinones such as N-methyl-2-oxazolidinone and mixtures thereof. Maximum conductivities of the electrolyte salts of this invention in typical nonaqueous, polar, aprotic liquid media (e.g., propylene carbonate) are generally in the range of 0.1–20 mS (milliSiemens) at room temperature, preferably greater than 1 mS.

A preferred electrochemical system of the present invention relates to a battery that includes at least one cathode, at least one anode, a separator and liquid electrolyte comprising certain fluorinated imide surfactant salts, conductive salts and aprotic solvents.

The electrodes (i.e., anode and cathode) of, for example, a lithium battery generally consist of a metallic foil or particles of active material blended with a conductive diluent such as carbon black or graphite bound into a plastic material binder. Typical binders include polytetrafluoroethylene, polyvinylidene fluoride, ethylene-propylene-diene (EPDM) terpolymer, and emulsified styrene-butadiene rubber (SBR), and the binder may be cross-linked. The binder may also be, for example, a solid carbon matrix formed from the thermal decomposition of an organic compound. The metallic foil or composite electrode material is generally applied to an expanded metal screen or metal foil (preferably aluminum, copper or nickel) current collector using a variety of processes such as coating, casting, pressing or extrusion.

Examples of suitable battery anodes include lithium metal, lithium metal alloys, sodium metal, carbon-based materials such as graphite, coke, carbon fiber, pitch, transition metal oxides (such as $LiTi_5O_{12}$ and $LiWO_2$), and lithiated tin oxide. In the case of lithium ion batteries, the lithium may be intercalated into a host material such as carbon (i.e., to give lithiated carbon) or carbon alloyed with other elements (such as silicon, boron and nitrogen), a conductive polymer, or an inorganic host that is intercalatable (such as $Li_xTi_5O_{12}$). The material comprising the anode may be carried on foil (e.g., nickel and copper) backing or pressed into expanded metal screen and alloyed with various other metals.

Examples of suitable cathode materials include graphite, amorphous carbon, $Li_xCoO_2$, $Li_xNiO_2$, Co-doped $Li_xNiO_2$, $Li_xMn_2O_4$, $Li_xMnO_2$, $V_2O_5$, $V_6O_{13}$, $LiV_3O_8$, $Ba_2SmNiO_5$, $SmMnO_3$, $Sm_3Fe_5O_{12}$, $EuFeO_3$, $EuFe_5O_{12}$, $EuMnO_3$, $LaNiO_3$, $La_2CoO_4$ and $LaMnO_3$ (including the charged and discharged forms of these materials), and conducting polymers such as polypyrrole, polysulfides and polyvinylferrocene. In primary batteries, the cathode can be fluorinated carbon (e.g., $(CF)_n$), $SO_2Cl_2$, $Ag_2V_4O_{11}$, $Ag_2CrO_4$, sulfur, polysulfide, and an $O_2$ or $SO_2$ electrode.

Lithium batteries and supercapacitors usually contain a separator to prevent short-circuiting between the cathode and anode. The separator usually consists of a single-ply or multi-ply sheet of microporous polymer (typically polyolefin, e.g., 30 polyethylene, polypropylene, or combinations thereof) having a predetermined length and width and having a thickness of less than 10 mils (0.025 cm). For example, see U.S. Pat. Nos. 3,351,495 (Larsen et al.), 4,539,256 (Shipman et al.), 4,731,304 (Lundquist et al.) and 5,565,281 (Yu et al.). The pore size in these microporous membranes, typically about 5 microns in diameter, is sufficiently large to allow transport of ions but is sufficiently small to prevent cathode/anode contact, either directly or from particle penetration or dendrites which can form on the electrodes.

The invention is illustrated further by, but is not intended to be limited to, the following examples.

EXAMPLES

Synthesis, Source of Fluorinated Imide Salts

$Li^+PF_6^-$ $Li^+PF_6^-$ (high purity, battery grade) was purchased from Hashimoto Chemical Co., Ltd. through Biesterfeld U.S., Inc., a U.S. distributor.

$CF_3SO_3^-Li^+$

Fluorad™ CF-122 Lithium Trifluoromethanesulfonate (available from 3M Co.) was used as the source of $CF_3SO_3^-Li^+$.

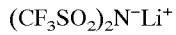
$(CF_3SO_2)_2N^-Li^+$

Fluorad™ HQ-115 Lithium Trifluoromethanesulfonimide (available from 3M Co.) was used as the source of $(CF_3SO_2)_2N^-Li^{30}$.

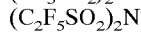
$(C_2F_5SO_2)_2N^-Li^+$ $(C_2F_5SO_2)_2N^-Li^+$ was prepared using the procedure described in Example 3 of U.S. Pat. No. 5,652,072, which is herein incorporated by reference.

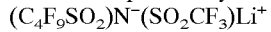
$(C_4F_9SO_2)N^-(SO_2CF_3)Li^+$ $(C_4F_9SO_2)N^-(SO_2CF_3)Li^+$ was prepared using the procedure described in Example 1 of U.S. Pat. No. 5,652,072, which is herein incorporated by reference.

$(C_8F_{17}SO_2)N^-(SO_2CF_3)Li^+$ $(C_8F_{17}SO_2)N^-(SO_2CF_3)Li^+$ was prepared using essentially the same procedure as described in Example 1 of U.S. Pat. No. 5,652,072, except that $C_8F_{17}SO_2F$ was substituted for $C_4F_9SO_2F$.

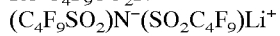
$(C_4F_9SO_2)N^-(SO_2C_4F_9)Li^+$ $(C_4F_9SO_2)N^-(SO_2C_4F_9)Li^+$ was prepared using the procedure described in Example 4 of U.S. Pat. No. 5,652,072, which is herein incorporated by reference.

$(C_8F_{17}SO_2)N^-(SO_2C_8F_{17})Li^+$ $(C_8F_{17}SO_2)N^-(SO_2C_8F_{17})Li^+$ was prepared using essentially the same procedure as described in Example 4 of U.S. Pat. No. 5,652,072, except that $C_8F_{17}SO_2F$ was substituted for $C_4F_9SO_2F$.

Battery Separators

The membranes employed in the following test methods were prepared as follows:

PP 1117-19 Membrane Preparation

A polypropylene resin, available from Union Carbide under a designation DS 5D45 with a melt flow index of 0.65 dg/min (ASTM D 1238, Condition I), was fed into the hopper of a 40 mm twin-screw extruder. Mineral oil, available under a trade designation Amoco White Mineral Oil #31 and having a viscosity of 60 centistokes (ASTM D445 at 40° C.) (available from Amoco Petroleum Products, Oak Brook, Ill.), was introduced into the extruder through an injection port at a rate to provide a composition of 60% by weight of the polymer and 40% by weight mineral oil. The composition also contained 0.28% Millad™ 3905 (available from Milliken & Co., Spartanburg, S.C.) nucleating agent. The overall feed rate was 11.35 kg/hr. The polymer was heated to 271° C. in the extruder to melt and, after mixing with oil, the temperature was maintained at 177° C. during the extrusion. The melt was extruded through a 38.1 cm-wide coat hanger slit die and cast onto a casting wheel maintained at 60° C. The cast film was extracted with HCFC-123 (LVertrel™ 423, $C_2HF_3Cl_2$, duPont) to remove mineral oil, then oriented 2.7 to 1 in the machine direction at 90° C. and 1.5 to 1 in the cross-direction at 138° C.

PE 9711Cotran Membrane Preparation

A polyethylene resin, available from Fina Chemicals under a designation Fina 1285 with a melt flow index of 8 dg/min (ASTM D1238-90, Condition F), was fed into the hopper of a 40 mm twin-screw extruder. Mineral oil, available under a trade designation Witco Protol and having a viscosity of 36 centistokes (ASTM D445 at 40° C.) (available from Witco Corp., Greenwich, Conn.) was introduced into the extruder through an injection port at a rate to provide a composition of 39% by weight of the polymer and 61% by weight mineral oil. The overall feed rate was 10.7 kg/hr. The polymer was heated to 271° C. in the extruder to melt and, after mixing with oil, the temperature was maintained at 204° C. during the extrusion. The melt was extruded through a 38.1 cm-wide coat hanger slit die and cast onto a casting wheel maintained at 66° C. The cast film was extracted with HCFC-123 to remove mineral oil, then oriented 2.3 to 1 in the machine direction at 35° C. and 2.2 to 1 in the cross-direction at 102° C.

Preparation of Electrodes

Cathode

A mix was prepared by blending 44 g of $LiCoO_2$ (FMC, Bessemer City, N.C.) with 5.0 g of VXC72 conductive carbon (Cabot Corp., Billesica, Mass.) and 1.0 g of Kynar 461 polyvinylidene fluoride resin (Elf Atochem North America, Philadelphia, Pa.) in a small food processor for 2 minutes. The food processor is a small single-speed common household food processor. Portions of the resulting mix were pressed into pellets using a pellet die and a Carver press at about 2000 pounds of force. The pellet die is a steel cylinder body 3 cm diameter by 2.5 cm height with a central bore 7.5 mm in diameter and a steel pin 3.75 cm in length and 7.47 cm in diameter with flat ends. The body of the die was placed on a flat surface and loaded with a measured weight of mix. The pin was inserted and the whole assembly placed in the Carver press. The resulting pellet electrodes averaged 7.6 mm in diameter, 0.28 mm in height and 33 mg in weight.

Anode

Anode pellets were prepared in a manner identical to the cathode procedure except that the ingredients of the mix were 21 g of XP3 petroleum coke (Conoco, Ponca City, Okla.), 1.2 g of Super S conductive carbon (MMM Carbon, Brussels, Belgium), and 3 g of Kynar 461 polyvinylidene fluoride. The resulting pellet electrodes averaged 7.7 mm in diameter, 0.35 mm in height and 27 mg in weight.

Test Methods

Surface Tension

Surface tensions of electrolytes were measured using the Wilhelmy plate method, which utilizes a vertically suspended roughened platinum plate of exactly known geometry. Using this method, the lower edge of the plate is brought into contact with the electrolyte, with the electrolyte "jumping" to (i.e., forming a meniscus along the side of) the plate and pulling the plate into the electrolyte. The Wilhelmy force along the length of the edge caused by this wetting is measured by pulling the plate from the electrolyte until the plate is level to the surface of the electrolyte. The surface tension, in dynes/cm, is then recorded as the force exerted by the electrolyte per length of plate edge contacted.

Coin Cell Charge/Discharge Cycling

To demonstrate electrolyte performance in a real test battery, charge/discharge cycling tests were run with a "1225" size coin cell, measuring capacity using a commercial battery tester available from Maccor Inc., Tulsa, Okla.

The "1225" coin cell stack assembly was constructed as shown in FIG. 1. A stainless steel top 1, 12 mm in diameter, was placed on a horizontal surface flat side down. On this base were stacked in order a 31 mil (0.80 mm) thick copper disk anode current collector 2 and an anode 3 prepared as described above. 40 μl of the test electrolyte solution (consisting of test salt(s) dissolved in a 50/50 (vol) blend of ethylene carbonate/dimethyl carbonate, dried to a water content of no greater than 50 ppm, as determined by Karl Fischer titration) was applied to the graphite side of the anode surface, then two layers of #9711 polyethylene, 2.2 mils, separator 4 (prepared as described above) were placed on the wet anode surface. A polypropylene spacer gasket 5 was inserted. To complete the assembly, cathode 6 prepared as described above was placed on the stack, 40 μl of additional electrolyte were added, followed by a 20 mil (0.51 mm) thick aluminum disk cathode current collector 7 and a chromium steel can cell 8. The assembly was then crimp sealed to complete the fabrication of the "1225" coin cell.

The constructed "1225" coin cell was then cycled at room temperature using a Maccor® Series 2000 battery tester (available from Maccor Inc., Tulsa Okla.) with appropriate current and voltage range operated with generation 3.0 software designed to charge the cell at a current density of no greater than 2 mA/cm$^2$ under a constant voltage of 4.2 V, followed by discharge under a constant current of 1 mA/cm$^2$, with two 30 minute interrupts (i.e., no current flow, circuit opened up) when the cell voltage reached 3.8 V and 3.0 V, respectively; total discharge time was typically 3 hours. Each cell was charged for a minimum of 10 cycles. Every fifth cycle the discharge current was scanned successively from a high of 30 mA/cm$^2$ to a low of 0.03 mA/cm$^2$, at a starting and ending potential of 4 V, in order to determine the rate capability and the maximum capacity of the cell. The average total cell discharge specific capacity (mAh/g) was plotted vs. cycle number. It is desirable that initial capacity be high and remain high over the entire number of cycles run. The impedance characteristics of the cells before cycling were determined using a Princeton Applied Research Model 271 potentiostat and a Solatron® FRA SI1260 frequency response analyzer equipped with an I1287 electrochemical interphase (both available from Solatron, a Division of Solatron Group Ltd., Houston, Tex.). Scans were made at an amplitude of 5 millivolts over a frequency range of 100,000 Hz to 0.1 Hz.

Repassivation Potential Test Procedure

The repassivation potential of the candidate salt was measured using a cyclic voltammetry test employing aluminum as a working electrode, using the technique generally described in Bard and Faulkner, Electrochemical Methods: Fundamentals and Applications, John Wiley and Sons, New York, 1980, pp. 350–353. The repassivation potential is an excellent predictor of the degree of corrosion to be expected when aluminum is used in an electrode, especially as a current collector.

For each cyclic voltammetry measurement, a three-electrode cell was used, having polished aluminum as the working electrode, metallic lithium as the reference electrode and platinum plate as the counter electrode. The aluminum electrode consisted of a 99.9% pure aluminum rod inserted into a polytetrafluoroethylene sleeve to provide a planar electrode having an area of 0.07 cm$^2$. Prior to running each cyclic voltammetry test, the native metal oxide layer was removed from the aluminum electrode by polishing the electrode with 3 μm aluminum oxide paper using heptane as a lubricant. A lithium wire inserted in a luggin glass capillary served as a reference electrode, and a 10 cm$^2$ platinum flag was used as the auxiliary electrode.

After polishing, the three electrodes and a glass cell for holding the electrolyte were all placed in an argon dry box (water and oxygen level less than 1 ppm), and the three electrodes were connected to a potentiostat. Each electrolyte salt to be evaluated was dissolved at 1 M concentration in a 1:1 (vol) blend of ethylene carbonate:dimethyl carbonate to form the test electrolyte (containing less than 50 ppm water, as determined by Karl Fischer titration), and 10 mL of each test electrolyte was placed in the glass cell. A scan at the rate of approximately 0.5 mV/sec was taken from 1 V up to at least 5 V (vs. the reference electrode), followed by gradually returning the potential to 4 V, and the current was measured as a function of voltage potential. The repassivation potential was defined as that voltage at which the measured current of the hysteresis loop fell precipitously back to a value close to the currents measured during the early part of the forward scan (i.e., the point of inflection on the curve). The corrosion current was also measured at each repassivation potential.

Examples 1–2 and Comparative Examples C11–C5

The wetting ability of various fluorinated imide surfactant salts, both inside and the outside of this invention, was evaluated by dissolving each salt at 1 molar concentration in a 50/50 (wt) blend of propylene carbonate/ethylene carbonate to form a liquid electrolyte, applying electrolyte to the surface of polyolefin separators, and then measuring contact angles, both initially and after 500 seconds of contact.

Separators used were 9711 Cotran polyethylene separator (prepared as above described) and 1117-19D polypropylene separator (prepared as above described). Contact angles were measured using a Kruss G2/G40 Contact Angle Measuring Device (available from Kruss Corp.).

Results from this contact angle evaluation are shown in Table 1.

TABLE 1

| | | | Polyethylene: | | Polypropylene: | |
|---|---|---|---|---|---|---|
| Ex. | Salt | No. of C Atoms: | Init. | 500 s. | Init. | 500 s. |
| 1 | $(C_8F_{17}SO_2)N^-(SO_2CF_3)Li^+$ | 9 | 47 | 0 | 47 | 39 |
| 2 | $(C_4F_9SO_2)N^-(SO_2C_4F_9)Li^+$ | 8 | 47 | 0 | 59 | 56 |
| C1 | $(C_4F_9SO_2)N^-(SO_2CF_3)Li^+$ | 5 | 41 | 0 | 76 | 69 |
| C2 | $(C_2F_5SO_2)N^-(SO_2C_2F_5)Li^+$ | 4 | 67 | 65 | 76 | 76 |
| C3 | $(CF_3SO_2)N^-(SO_2CF_3)Li^+$ | 2 | 87 | 87 | 84 | 84 |
| C4 | $CF_3SO_3^-Li^+$ | 1 | 79 | 73 | 83 | 83 |
| C5 | $Li^+PF_6^-$ | 0 | 77 | 73 | 79 | 79 |

The data in Table 1 show that, with the polyethylene separator, the imide salts having at least 8 carbons in their combined perfluorinated chains provided a liquid electrolyte with superior wetting performance, particularly after contact for 500 seconds. A lesser wetting improvement was noted with the polypropylene separator.

Example 3

$(C_8F_{17}SO_2)N^-(SO_2CF_3)Li^+$ surfactant salt was evaluated as an additive to a liquid electrolyte to enhance the electrolyte's wetting of a porous polypropylene separator.

In Example 3, 0.15 g of $(C_8F_{17}SO_2)N^-(SO_2CF_3)Li^+$ was added to 5 g of a 1 M solution of $(CF_3SO_2)N^-(SO_2CF_3)Li^+$ (HQ-115) in anhydrous propylene carbonate. 3 drops of the resulting solution were placed on a Celgard™ 2400 porous polypropylene separator (available from Hoechst Celanese Corp., Charlotte, N.C.). The drops initially beaded up but gradually penetrated the pores of the separator, causing the separator to change in appearance from opaque to translucent.

Examples 4–6 and Comparative Examples C6–C7

This exothermic energy test was run to simulate the Underwriter's Laboratory hot box test, which measures a battery's performance after exposure to 150° C. storage conditions. Specifically, $(C_8F_{17}SO_2)N^-(SO_2CF_3)Li^+$ (MOI, Ex. 4), $(C_4F_9SO_2)N^-(SO_2C_4F_9)Li^+$ (DBI, Ex. 5) and $(C_8F_{17}SO_2)N^-(SO_2C_8F_{17})Li^+$ (DOI, Ex. 6) were evaluated as additives to an electrolyte containing $(C_2F_5SO_2)_2N^-Li^+$ (BETI) to determine their effect on exothermic energies measured up to 200° C. in a half-cell "1225" coin cell—relative to control electrolytes containing BETI (Comparative Example C6) or $Li^+PF_6^-$ (Comparative Example C7).

The half-cell "1225" coin cell used for this set of experiments was constructed as follows. Lithium metal was used as the anode and SFG44 graphite was used as the cathode. The SFG44 cathode composition, consisting of 85% (wt) SFG44 graphite (available from Timcal Co., West Lake, Ohio), 3% (wt) Super P (available from MMM carbon, Antwerp, Belgium), 12% (wt) polyvinylidene fluoride resin (PVDF) (available from Elf Atochem North America) and 0.1% (wt) oxalic acid, was coated onto a copper substrate, dried at 120° C. under vacuum for 12 hours, and was cut into circular disks having an area of 0.44 cm². Electrolyte solutions were prepared by dissolving dry conductive salts (either BETI or $LiPF_6$, having a water content of less than 30 ppm as determined by Karl Fisher titration) at 1M concentration in a dry solvent blend consisting of 50/50 (vol/vol) ethylene carbonate/dimethyl carbonate (available from Grant Chemicals, San Leandro, Calif.). Each surfactant salt was added to a 1M BETI electrolyte at 10% by weight based on the weight of the conductive salt. Coin cells were then assembled in the following order: (1) stainless steel can top, (2) copper current collector, (3) lithium anode, (4) PE 9711 Cotran membrane, (5) polypropylene gasket, (6) about 30 µL of electrolyte, (7) SFG 44 cathode, (8) copper current collector and (9) stainless steel can bottom. Graphite lithiation was done by a discharge, charge, and final discharge process. Each cell was then stored for 24 hours at room temperature to achieve equilibrium. A constant current discharge and charge of 0.45 mA/cm² with voltage limits of 0.0 V and 2.0 V, respectively, was utilized.

After the discharge/charge/discharge cycle was run, each coin cell was taken to an Argon-filled dry box and the lithiated graphite electrodes were removed and cut into circular samples 2.9 mm in diameter. The pieces were weighed and then placed into sealed aluminum sample pans, and the pans with samples were transferred to an Argon-filled differential scanning calorimetry (DSC) chamber. DSC measurements were conducted at a 10° C./min heating rate from room temperature (usually about 27° C.) up to 500° C.

From the DSC data for each electrolyte, the total exothermic energy (in mJ/mg) released from 120° C. to 200° C. was determined as follows. For each electrolyte, the DSC scan graph was cropped to include only the 120° C. to 200° C. exotherm region. The cropped exotherm region was then weighed, and the weight ratio between each of the scan graphs and the corresponding scan graph for $LiPF_6$ was determined. Two overlapping test series were run, and the data were combined for presentation in Table 2.

TABLE 2

| Ex. | Surfactant Salt | Conductive Salt | Exotherm Energy Ratio Relative to $LiPF_6$ |
|---|---|---|---|
| 4 | MOI | BETI | 0.39[1] |
| 5 | DBI | BETI | 0.57[1] |
| 6 | DOI | BETI | 0.49[2] |
| C6 | — | BETI | 1.36[1] |
|  |  |  | 1.41[2] |
| C7 | — | $LiPF_6$ | 1.0[1] |
|  |  |  | 1.0[2] |

[1] Run in first test series
[2] Run in second test series

The data in Table 2 show that the addition of each surfactant salt to the 1M BETI electrolyte greatly decreased the amount of exothermic energy released, down to about half the level released when 1M $LiPF_6$ was used as the electrolyte.

Example 7–11 and Comparative Examples C8–C9

This series of examples was run to demonstrate the improved repassivation potential achieved when various bis(perfluoroalkanesulfonylimide) surfactant salts are incorporated into an electrolyte comprising a short chain bis(perfluoroalkanesulfonylimide) conductive salt.

In Examples 7–11, $(C_8F_{17}SO_2)N^-(SO_2CF_3)Li^+$, $(C_4F_9SO_2)N^-(SO_2C_4F_9)Li^+$ and $(C_8F_{17}SO_2)N^-(SO_2C_8F_{17})Li^+$ were added to 1M $(C_2F_5SO_2)_2N^-Li^+$ in a 50/50 (vol) blend of ethylene carbonate/dimethyl carbonate, at various concentrations by weight of conductive salt. The repassivation potential and corrosion current was measured for each electrolyte as described in the Repassivation Potential Test Procedure.

In Comparative Example C8, the repassivation potential for 1M $(C_2F_5SO_2)_2N^-Li^+$ in a 50/50 (vol) blend of ethylene carbonate/dimethyl carbonate was measured (i.e., no surfactant salt was added to the electrolyte).

In Comparative Example C9, the repassivation potential for 1M $Li^+PF_6^-$ in a 50/50 (vol) blend of ethylene carbonate/dimethyl carbonate was measured (i.e., no surfactant salt was added to the electrolyte).

Results are presented in Table 3.

TABLE 3

| Ex. | Cond. Salt, Name | Surfactant Salt: Name | Surfactant Salt: % (wt) | Repass. Potent. (V) | Corrosion Curr. (µA) |
|---|---|---|---|---|---|
| 7 | BETI | MOI | 3 | 4.50 | 70 |
| 8 | BETI | MOI | 7 | 4.58 | 30 |
| 9 | BETI | MOI | 10 | 4.61 | 18 |

TABLE 3-continued

| Ex. | Cond. Salt, Name | Surfactant Salt: Name | % (wt) | Repass. Potent. (V) | Corrosion Curr. ($\mu$A) |
|---|---|---|---|---|---|
| 10 | BETI | DBI | 10 | 4.47 | 73 |
| 11 | BETI | DOI | 10 | 4.65 | 1.1 |
| C8 | BETI | — | — | 4.43 | 350 |
| C9 | LiPF$_6$ | — | — | >6 | 0 |

The data in Table 3 show that addition of the surfactant salt to the BETI salt in the electrolyte improved repassivation potential and corrosion current of the BETI salt used alone in the electrolyte. The performance of the BETI electrolytes containing 10% surfactant salts having at least one C$_8$ chain (MOI, DOI) approached the performance of the LiPF$_6$ electrolyte.

Example 12–24 and Comparative Example C10–C17

This series of examples was run to demonstrate the improved capacity fade performance achieved when various bis(perfluoroalkanesulfonylimide) surfactant salts are incorporated into an electrolyte comprising a short chain bis (perfluoroalkanesulfonylimide) conductive salt.

A "1225" coin cell stack was assembled as described in the Coin Cell Charge/Discharge Cycling test procedure. The cathode was constructed from a mixture consisting of the following components (% by weight): 83% LiCoO2, 2.5% Super P, 12% PVDF and 2.5% KF6 (a flaked graphite available from Timcal Co.). An anode was constructed consisting from a mixture of the following components (% by weight): 85% SFG44 Graphite, 3% Super P, 12% PVDF and 0.1% oxalic acid. 30 $\mu$L of electrolyte was used in each cell. Cycling to measure capacity fade was done between room temperature and 60° C., including a 72 hour storage step at full charge. Charging was done under a constant voltage of 4.2 V, beginning with a current limit of 2 mA/cm$^2$ and terminating when the current fell to 0.26 mA/cm$^2$. Discharging was done under a constant current of 1.32 mA/cm$^2$ with a voltage termination of 2.75 V.

For a given electrolyte formulation, the cells were cycled 15 times at room temperature. Then the cells were brought to 60° C. and two cycles were run at charge (4.2 V) and discharge (open circuit for 72 hours—full charge storage). After the 72 hour storage period at 60° C. with open circuit, the cells were discharged and two additional charge/discharge cycles were run at 60° C. under the same current rate and limited voltage conditions as were run during the 15 cycles at room temperature. The cells were then returned to room temperature and cycled again at least 5 times at room temperature. The process of cycling and storage at 60° C. followed by cycling at room temperature was repeated 6 times (i.e., 6 "macrocycles") for each electrolyte combination, and the % capacity retention after the second up to the sixth macrocycle was calculated as a percentage of discharge capacity (mAh/g) measured after the first cycle.

Results are presented in Table 4.

TABLE 4

| Ex. | Cond. Salt | Surfactant Salt: Name | % (wt) | Capacity Retention After: Macrocycle | % |
|---|---|---|---|---|---|
| 12 | BETI | MOI | 3 | 2 | 37 |
| 13 | BETI | MOI | 3 | 3 | 27 |
| 14 | BETI | MOI | 3 | 4 | 6 |
| 15 | BETI | MOI | 7 | 2 | 61 |
| 16 | BETI | MOI | 7 | 3 | 58 |
| 17 | BETI | MOI | 10 | 2 | 71 |
| 18 | BETI | MOI | 10 | 3 | 68 |
| 19 | BETI | MOI | 10 | 4 | 71 |
| 20 | BETI | MOI | 10 | 5 | 66 |
| 21 | BETI | MOI | 10 | 6 | 67 |
| 22 | BETI | MOI | 20 | 2 | 72 |
| 23 | BETI | MOI | 20 | 3 | 63 |
| 24 | BETI | MOI | 20 | 4 | 68 |
| C10 | BETI | — | — | 2 | 38 |
| C11 | BETI | — | — | 3 | 4 |
| C12 | BETI | — | — | 4 | 0 |
| C13 | LiPF$_6$ | — | — | 2 | 80 |
| C14 | LiPF$_6$ | — | — | 3 | 69 |
| C15 | LiPF$_6$ | — | — | 4 | 76 |
| C16 | LiPF$_6$ | — | — | 5 | 64 |
| C17 | LiPF$_6$ | — | — | 6 | 60 |

The data in Table 4 show that addition of the surfactant salt MOI to electrolyte containing BETI imparts to the coin cell a significant improvement in capacity retention, thus bringing the high temperature capacity fade performance of the BETI electrolyte salt to the level exhibited by the LiPF$_6$ electrolyte salt.

We claim:

1. An electrolyte composition comprising:

(a) a conductive salt comprising a cation selected from the group consisting of an alkali metal; an alkaline earth metal; a Group IIB metal; a Group IIIB metal; a transition metal; a rare earth metal; a nitrogen onium cation, and a proton; and an anion selected from the group consisting of $R_f^0SO_3^-$; in which $R_f^0$ is a perfluoroalkyl group having between 2 and 4 carbon atoms;

an anion of the formula:

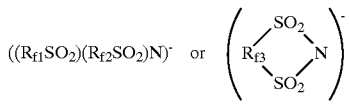

in which $R_{f1}$ and $R_{f2}$ are each independently a straight or branched perfluoroalkyl group of 1 to 4 carbon atoms, with $R_{f1}$ and $R_{f2}$ having a total of up to 5 carbon atoms;

and $R_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms;

an anion having a formula $R_{f4}R_{f5}N\text{—}(CF_2)_n\text{'}SO_2\text{—}X$;

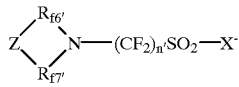

in which X⁻ is —O⁻, —N⁻SO$_2$R$_{f4}$, or

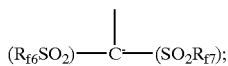

Z is —CF$_2$—, —O—,

or —SF$_4$—; R$_{f4}$, R$_{f4'}$, and R$_{f5}$, independently, are —C$_m$F$_{2m+1}$ or —(CF$_2$)$_q$—SO$_2$—X⁻; R$_{f6}$ and R$_{f7}$, independently, are —C$_m$F$_{2m+1}$, —(CF$_2$)$_4$—SO$_2$—X⁻,

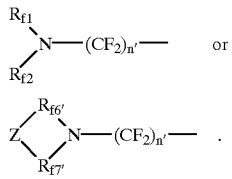

R$_{f8}$ is —C$_m$F$_{2m+1}$, or —(CF$_2$)$_q$—SO$_2$—X⁻; R$_{f6'}$ and R$_{f7'}$, independently, are perfluoroalkylene moieties having the formula —C$_r$F$_{2r}$—; n' is 1–4; r is 1–4; m is 1–4; and q is 1–4;

a bis-fluoroalkylsulfonyl methide anion R$_f^{II}$—SO$_2$—C⁻(R)—SO$_2$—R$_f^{III}$ in which R$_f^{II}$ and R$_f^{III}$, independently, are perfluoroalkyl groups having between 1 and 4 carbon atoms, wherein the sum of R$_4^{II}$ and R$_f^{III}$ is up to 5 carbon atoms, and R is H, CN, F, alkyl of 1 to 6 carbon atoms, phenyl or phenyl substituted by alkyl of 1 to 4 carbon atoms;

and a tris-(perfluoroalkanesulfonyl)methide anion of the formula $^{-C(SO}$$_2$R$_f^{II}$)(SO$_2$R$_f^{III}$)(SO$_2$R$_f^{IV}$) in which R$_f^{II}$, R$_f^{III}$, and R$_f^{IV}$, independently, are perfluoroalkyl groups having between 1 and 4 carbon atoms, wherein the sum of R$_f^{II}$, R$_f^{III}$ and R$_f^{IV}$ are up to 6 carbon atoms; and (b) a surfactant salt of the formula:

wherein M$^{+n}$ is a cation with a valence equal to n;
n is from 1 to 4;
R$_f$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms on the alkyl chain, which perfluoroalkyl or perfluorocycloalkyl chain may optionally contain catenary heteroatoms; and
R$_f'$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms on the alkyl chain, which perfluoroalkyl or perfluorocycloalkyl chain may optionally contain catenary heteroatoms; wherein R$_f$ and R$_f'$ have a total of at least 8 carbon atoms; and
wherein the molar ratio of conductive salt to surfactant salt is between about 99.9:0.1 to about 75:25.

2. The composition of claim 1, wherein R$_f$ is a straight or branched perfluoroalkyl group of 4 to 12 carbon atoms, and R$_f'$ is a straight or branched perfluoroalkyl group of 1 to 8 carbon atoms.

3. The composition of claim 1, wherein R$_f$ has at least 8 carbon atoms.

4. The composition of claim 1, wherein the surfactant salt has a cation M$^+$n selected from the group consisting of an alkali metal, an alkaline earth metal, a transition metal, a rare earth metal, a group IIB metal, a Group IIIB metal, tetraalkylammonium, N-alkylpyridinium and N,N'-dialkylimidazolium.

5. The composition of claim 4, wherein the cation is selected from the group consisting of Li$^+$, Na$^+$, Ca$^{+2}$, Ba$^{+2}$, Al$^{+3}$, Eu$^{+3}$, Sm$^{+3}$, (C$_2$H$_5$)$_4$N$^+$, (CH$_3$)$_4$N$^+$,

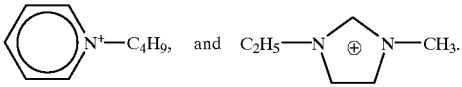

6. The composition of claim 1, wherein the surfactant salt is a member selected from the group consisting of (C$_8$F$_{17}$SO$_2$)N⁻(SO$_2$CF$_3$) Li$^+$, (C$_4$F$_9$SO$_2$)$_2$N⁻Li$^+$, (C$_8$F$_{17}$SO$_2$)$_2$N⁻Li$^+$, (C$_8$F$_{17}$SO$_2$)N⁻, (SO$_2$C$_4$F$_9$) Li$^+$, and ((CF$_3$)$_2$NCF$_2$CF$_2$SO$_2$)$_2$N⁻Li$^+$.

7. The composition of claim 1, wherein the molar ratio of conductive salt to surfactant salt is between about 99:1 and about 90:10.

8. The composition of claim 1, wherein the conductive salt has a (CF$_3$SO$_2$)$_3$C⁻ anion, or has an anion of the formula:

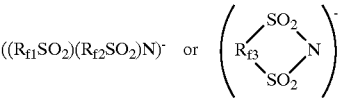

or has an anion of the formula:

in which R$_{f1}$ and R$_{f2}$ are each independently a straight or branched perfluoroalkyl group of 1 to 4 carbon atoms, with R$_{f1}$ and R$_{f2}$ having a total of up to 5 carbon atoms;

R$_{f3}$ is a perfluoroalkylene moiety of 2 to 4 carbon atoms optionally substituted by a straight or branched perfluoroalkyl group of 1 to 2 carbon atoms, with R$_{f3}$ having a total of up to 4 carbon atoms; and R$_f^V$ is a perfluoroalkyl group having from 2 to 4 carbon atoms.

9. The composition of claim 1, wherein the conductive salt is a member selected from the group consisting of lithium bis(perfluoromethanesulfonyl)imide, lithium perfluoroethanesulfonate, lithium tris (perfluoromethanesulfonyl)methide, lithium bis (perfluoroethanesulfonyl)imide, lithium (perfluorobutanesulfonyl)(per-fluoromethanesulfonyl) imide, lithium perfluorobutane sulfonate, and a mixture thereof.

10. The composition of claim 1, wherein the conductive salt has an anion of the formula:

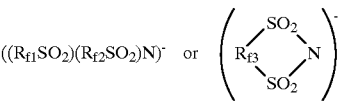

in which R$_{f1}$ and R$_{f2}$ are each independently a straight or branched perfluoroalkyl group of 1 to 4 carbon atoms, with R$_{f1}$ and R$_{f2}$ having a total of up to 5 carbon atoms; R$_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms.

11. The composition of claim 1, wherein the conductive salt is lithium bis(perfluoroethanesulfonyl)imide.

12. An electrochemical system comprising:
   at least one positive electrode;
   at least one negative electrode; and
   an electrolyte composition comprising:
   (a) a conductive salt comprising:
   a cation selected from the group consisting of an alkali metal; an alkaline earth metal; a Group IIB metal; a Group IIIB metal; a transition metal; a rare earth metal; a nitrogen onium cation, and a proton; and
   an anion selected from the group consisting of $R_f^0SO_3^-$; in which $R_f^0$ is a perfluoroalkyl group having between 2 and 4 carbon atoms;
   an anion of the formula:

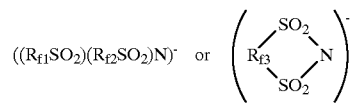

in which $R_{f1}$ and $R_{f2}$ are each independently a straight or branched perfluoroalkyl group of 1 to 4 carbon atoms, with $R_{f1}$ and $R_{f2}$ having a total of 5 carbon atoms; and $R_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms;
   an anion having a formula $R_{f4}R_{f5}N-(CH_2)_n\cdot SO_2-X$;

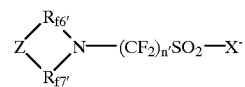

in which $X^-$ is $-O^-$, $-N^-SO_2R_{f4'}$ or

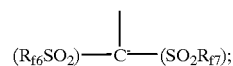

Z is $-CF_2-$, $-O-$,

or $-SF_4-$; $R_{f4}$, $R_{f4'}$ and $R_{f5}$, independently, are $-C_mF_{2m+1}$, or $-(CF_2)_q-SO_2-X^-$; $R_{f6}$ and $R_{f7}$, independently, are $-C_mF_{2m+1}-(CF_2)_4-SO_2-X^-$;

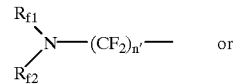

-continued

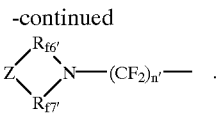

$R_{f8}$ is $-C_mF_{2m+1}$, or $-(CF_2)_q-SO_2-X^-$; $R_{f6'}$, and $R_{f7'}$, independently, are perfluoroalkylene moieties having the formula $-C_rF_{2r}-$; n' is 1–4; r is 1–4; m is 1–4; and q is 1–4;
   a bis-fluoroalkylsulfonyl methide anion $R_f^{II}-SO_2-C^-(R)-SO_2-R_f^{III}$ in which $R_f^{II}$ and $R_f^{III}$, independently, are perfluoroalkyl groups having between 1 and 4 carbon atoms, wherein the sum of $R_f^{II}$ and $R_f^{III}$ is up to 5 carbon atoms, and R is H, CN, F, alkyl of 1 to 6 carbon atoms, phenyl or phenyl substituted by alkyl of 1 to 4 carbon atoms;
   and a tris-(perfluoroalkanesulfonyl)methide anion of the formula $^-C(SO_2R_f^{II})(SO_2R_f^{III})(SO_2R_f^{IV})$ in which $R_f^{II}$, $R_f^{III}$, and $R_f^{IV}$, independently, are perfluoroalkyl groups having between 1 and 4 carbon atoms, wherein the sum of $R_f^{II}$, $R_f^{III}$ and $R_f^{IV}$ are up to 6 carbon atoms; and
   (b) a surfactant salt of the formula:

$$((R_fSO_2)(R_f'SO_2)N^-)_nM^{+n}$$

wherein $M^{+n}$ is a cation with a valence equal to n;
   n is from 1 to 4;
   $R_f$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms in the alkyl chain, which perfluoroalkyl or perfluorocycloalkyl chain may optionally contain catenary heteroatoms; and
   $R_f'$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms in the alkyl chain, which perfluoroalkyl or perfluorocycloalkyl chain may optionally contain catenary heteroatoms, wherein $R_f$ and $R_f'$ have a total of at least 8 carbon atoms; and
   wherein the molar ratio of conductive salt to surfactant salt is between about 99.9:0.1 to about 75:25.

13. The system of claim 12, which further comprises a non-aqueous matrix material.

14. The system of claim 12, wherein the molar ratio of conductive salt to surfactant salt is between about 99:1 and about 90:10.

15. The system of claim 12, wherein the surfactant salt has a cation $M^{+n}$ selected from the group consisting of an alkali metal, an alkaline earth metal, a transition metal, a rare earth metal, a group IIB metal, a Group IIIB metal, tetraalkylammonium, trialkylammonium, N-alkylpyridinium, N,N'-dialkylimidazolium, and a proton.

16. The system of claim 15, wherein the cation is selected from the group consisting of $Li^+$, $Na^+$, $Ca^{+2}$, $Ba^{+2}$, $Al^{+3}$, $Eu^{+3}$, $Sm^{+3}$, $(C_2H_5)_4N^+$, $(CH_3)_4N^+$,

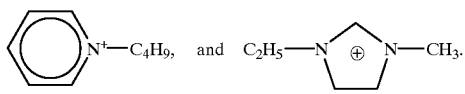

17. The system of claim 12, wherein the surfactant salt is a member selected from the group consisting of $(C_8F_{17}SO_2)$ $N^-(SO_2CF_3)Li^+$, $(C_4F_9SO_2)_2N^-Li^+$, $(C_8F_{17}SO_2)N^-(SO_2C_4F_9)Li^+$, $(C_8F_{17}SO_2)_2N^-Li^+$, and $((CF_3)_2NCF_2CF_2SO_2)_2N^-Li^+$.

18. The system of claim 12, wherein the electrolyte composition comprises:

(a) a conductive salt at a concentration from about 0.5 to 1.5 mole per liter; and (b) a surfactant salt at a concentration from about 10 to 100 millimole per liter.

19. The system of claim 12, wherein the conductive salt has a $(CF_3SO_2)_3C^-$ anion, or has an anion of the formula:

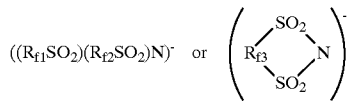

or has an anion of the formula:

in which $R_{f1}$ and $R_{f2}$ are each independently a straight or branched perfluoroalkyl group of 1 to 4 carbon atoms, with $R_{f1}$ and $R_{f2}$ having a total of up to 5 carbon atoms;

$R_{f1}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms; and $R_f^V$ is a perfluoroalkyl group having from 2 to 4 carbon atoms.

20. The system of claim 12, wherein the conductive salt is lithium bis(perfluoroethanesulfonyl)imide.

21. The system of claim 12, being a battery or rechargeable battery.

22. The battery or rechargeable battery of claim 21, comprising a lithium-intercalated carbon anode and a metal oxide cathode.

23. A method of improving safety and performance of an electrochemical system which comprises using an electrolyte composition in said system comprising:

(a) an effective amount of a surfactant salt of the formula

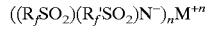

wherein $M^{+n}$ is a cation with a valence equal to n;

n is from 1 to 4;

$R_f$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms in the alkyl chain, which perfluoroalkyl or perfluorocycloalkyl chain may optionally contain catenary heteroatoms; and $R_f'$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms in the alkyl chain, which perfluoroalkyl or perfluorocycloalkyl chain may optionally contain catenary heteroatoms, wherein $R_f$ and $R_f'$ have a total of at least 8 carbon atoms; and (b) a conductive salt having a cation selected from the group consisting of an alkali metal; an alkaline earth metal; a Group IIB metal; a Group IIIB metal; a transition metal; a rare earth metal; a nitrogen onium cation; and a proton; and an anion of the formula

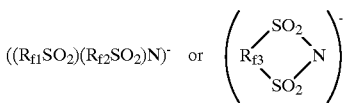

in which $R_{f1}$ and $R_{f2}$ are each independently a straight or branched perfluoroalkyl group of 1 to 4 carbon atoms, with $R_{f1}$ and $R_{f2}$ having a total of up to 5 carbon atoms; $R_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms; and a matrix material.

24. The method of claim 23, wherein the system is a battery or rechargeable battery.

25. The method of claim 23, wherein the system is a lithium battery.

26. The method of claim 23, wherein the electrolyte composition comprises 10% by weight or more of the surfactant salt based on the weight of the conductive salt.

27. An electrochemical system comprising:

at least one positive electrode;

at least one negative electrode; and an electrolyte composition comprising in a non-aqueous matrix material:

(a) a conductive salt having a cation selected from the group consisting of an alkali metal; an alkaline earth metal; a Group IIB metal; a Group IIIB metal; a transition metal; a rare earth metal; a nitrogen onium cation; and a proton; and an anion of the formula

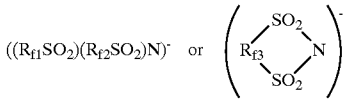

in which $R_{f1}$ and $R_{f2}$ are each independently a straight or branched perfluoroalkyl group of 1 to 4 carbon atoms, with $R_{f1}$ and $R_{f2}$ having a total of up to 5 carbon atoms; $R_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms; and (b) an effective amount of a surfactant salt of the formula

wherein $M^{+n}$ is a cation with a valence equal to n;

n is from 1 to 4;

$R_f$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms in the alkyl chain, which perfluoroalkyl or perfluorocycloalkyl chain may optionally contain catenary heteroatoms; and $R_f'$ is a straight or branched perfluoroalkyl group of 1 to 8 carbon atoms, a perfluorocycloalkyl group or a perfluorocycloalkyl perfluoroalkyl group of 4–7 ring carbon atoms and 1–4 carbon atoms in the alkyl chain, which perfluoroalkyl or perfluorocycloalkyl chain may optionally contain catenary heteroatoms, wherein $R_f$ and $R_f'$ have a total of at least 8 carbon atoms.

28. The system of claim 27, wherein the electrolyte composition comprises 10% by weight or more of the surfactant salt based on the weight of the conductive salt.

29. The system of claim 27, wherein the surfactant salt is a member selected from the group consisting of $(C_8F_{17}SO_2)N^-(SO_2CF_3)Li^+$, $(C_4F_9SO_2)_2N^-Li^+$, $(C_8F_{17}SO_2)N^-(SO_2C_4F_9)Li^+$, $(C_8F_{17}SO_2)_2N^-Li^+$, and $((CF_3)_2NCF_2CF_2SO_2)_2N^-Li^+$.

30. The system of claim 27, wherein the conductive salt has a lithium cation.

31. The system of claim 27, wherein the conductive salt is lithium bis(perfluoroethanesulfonyl)imide.

32. The system of claim 27, being a battery or rechargeable battery.

33. The battery or rechargeable battery of claim 32, comprising a lithium-intercalated carbon anode and a metal oxide cathode.

34. An electrolyte composition comprising in a matrix material:

(a) a conductive salt having a cation selected from the group consisting of an alkali metal; an alkaline earth metal; a Group IIB metal; a Group IIIB metal; a transition metal; a rare earth metal; a nitrogen onium cation; and a proton; and an anion of the formula:

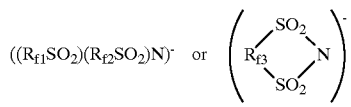

in which $R_{f1}$ and $R_{f2}$ are each independently a straight or branched perfluoroalkyl group of 1 to 4 carbon atoms, with $R_{f1}$ and $R_{f2}$ having a total of up to 5 carbon atoms; $R_{f3}$ is a perfluoroalkylene moiety of 2 to 4 carbon atoms optionally substituted by a straight or branched perfluoroalkyl group of 1 to 2 carbon atoms, with $R_{f3}$ having a total of up to 4 carbon atoms; and (b) a surfactant salt of the formula $((R_fSO_2)(R_f'SO_2)N^-)_nM^{+n}$ wherein $M^{+n}$ is a cation with a valence equal to n;

n is from 1 to 4;

$R_f$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms in the alkyl chain, which perfluoroalkyl or perfluorocycloalkyl chain may optionally contain catenary heteroatoms; and $R_f'$ is a straight or branched perfluoroalkyl group of 1 to 12 carbon atoms, a perfluorocycloalkyl group or a perfluorocycloalkyl perfluoroalkyl group of 4–7 ring carbon atoms and 1–4 carbon atoms in the alkyl chain, which perfluoroalkyl or perfluorocycloalkyl chain may optionally contain catenary heteroatoms, wherein $R_f$ and $R_f'$ have a total of at least 8 carbon atoms.

35. The composition of claim 34, wherein the conductive salt has a lithium cation.

36. The composition of claim 34, wherein the conductive salt is lithium bis(perfluoroethanesulfonyl)imide.

37. The composition of claim 34, wherein $R_f$ has at least 8 carbon atoms.

38. The composition of claim 34, wherein the surfactant salt has a cation $M^{+n}$ selected from the group consisting of an alkali metal, an alkaline earth metal, a transition metal, a rare earth metal, a group IIB metal, a Group IIIB metal, tetraalkylammonium, N-alkylpyridinium and N,N'-dialkylimidazolium.

39. The composition of claim 34, wherein the surfactant salt has a lithium cation.

40. The composition of claim 34, wherein the surfactant salt is a member selected from the group consisting of $(C8F_{17}SO_2)N^-(SO_2CF_3)Li^+$, $(C_4F_9SO_2)_2N^-Li^+$, $(C_8F_{17}SO_2)N^-(SO_2C_4F_9)Li^+$, $(C_8F_{17}SO_2)_2N^-Li^+$, and $((CF_3)_2NCF_2CF_2SO_2)_2N^-Li^+$.

41. The composition of claim 34, wherein the surfactant salt comprises 10% by weight or more of the composition based on the weight of the conductive salt.

* * * * *

UNITED STATES PATENT AND TRADEMARK OFFICE
CERTIFICATE OF CORRECTION

PATENT NO. : 6,280,883 B1
DATED : August 28, 2001
INVENTOR(S) : Lamanna, William M.

It is certified that error appears in the above-identified patent and that said Letters Patent is hereby corrected as shown below:

Column 3,
Line 57, "(R)—SO$_2$—R$_f^{II}$" should read -- (R)—SO$_2$—R$_f^{III}$ --;

Column 11,
Line 39, "(CF$_3$SO$_2$)$_2$N—Li$^{30}$" should read -- (CF$_3$SO$_2$)$_2$N—Li$^+$ --;

Column 14,
Line 36, "Examples C11-C5" should read -- Examples C1-C5 --;

Column 19,
Line 37, "—C(SO$_2$R$_f^{II}$)" should read -- —C(SO$_2$R$_f^{II}$) --;

Column 20,
Line 2, "M$^+$n" should read -- M$^{+n}$ --;

Column 23,
Line 2, "(SO2C$_4$F$_9$)" should read -- (SO$_2$C$_4$F$_9$) --;
Line 26, "R$_{fl}$" should read -- R$_{f3}$ --; and Column 26,
Line 33, "(C8F$_{17}$SO$_2$)" should read -- (C$_8$F$_{17}$SO$_2$) --.

Signed and Sealed this

Twenty-eighth Day of May, 2002

Attest:

*Attesting Officer*

JAMES E. ROGAN
*Director of the United States Patent and Trademark Office*